United States Patent [19]

Williams et al.

[11] Patent Number: 5,303,578
[45] Date of Patent: Apr. 19, 1994

[54] RHEOMETER

[75] Inventors: Phylip R. Williams, Penard; David J. A. Williams, Swansea, both of United Kingdom

[73] Assignee: Carri-Med Limited, Surrey, United Kingdom

[21] Appl. No.: 867,665

[22] PCT Filed: Nov. 2, 1990

[86] PCT No.: PCT/GB90/01691
§ 371 Date: Jul. 3, 1992
§ 102(e) Date: Jul. 3, 1992

[87] PCT Pub. No.: WO91/06842
PCT Pub. Date: May 16, 1991

[30] Foreign Application Priority Data

Nov. 3, 1989 [GB] United Kingdom ............... 8924851

[51] Int. Cl.$^5$ ............................ G01N 11/14
[52] U.S. Cl. .................. 73/54.24; 73/54.23; 73/54.28; 73/54.37; 73/54.39
[58] Field of Search ............ 73/54.39, 54.23, 54.24, 73/54.28, 54.37

[56] References Cited

U.S. PATENT DOCUMENTS

| | | | |
|---|---|---|---|
| 3,611,789 | 10/1971 | Lopas | 73/54.28 |
| 3,943,753 | 3/1976 | Simon | 73/54.23 |
| 4,148,214 | 4/1979 | Madsen | 73/54.23 |
| 4,488,427 | 12/1984 | Matusik et al. | 73/54.23 |
| 4,535,621 | 8/1985 | Gervais et al. | 73/54.23 |
| 4,566,324 | 1/1986 | Vinogradov et al. | 73/54.39 |
| 5,056,358 | 10/1991 | Laskowski et al. | 73/54.28 |

FOREIGN PATENT DOCUMENTS

| | | | |
|---|---|---|---|
| 0216103 | 11/1984 | Fed. Rep. of Germany | 73/54.23 |
| 0517833 | 6/1976 | U.S.S.R. | 73/54.39 |
| 0570517 | 8/1977 | U.S.S.R. | 73/54.39 |
| 1608497 | 11/1990 | U.S.S.R. | 73/54.23 |

*Primary Examiner*—James C. Housel
*Assistant Examiner*—Laura E. Collins
*Attorney, Agent, or Firm*—David P. Gordon

[57] ABSTRACT

Apparatus and a method for investigating dynamic rheological properties of a viscoelastic medium involves oscillating at least one shear wave generation surface in a container containing the viscoelastic medium such that shear waves generated thereby impinge on two spaced shear wave receiving surfaces, the receiving surfaces being spaced by different distances from the source of shear waves impinging thereon. Transducers are provided for the shear wave receiving surfaces capable of generating output signals dependent on the variations in physical parameters of heating the wave receiving surfaces induced by the oscillating shear wave generation surfaces.

22 Claims, 1 Drawing Sheet

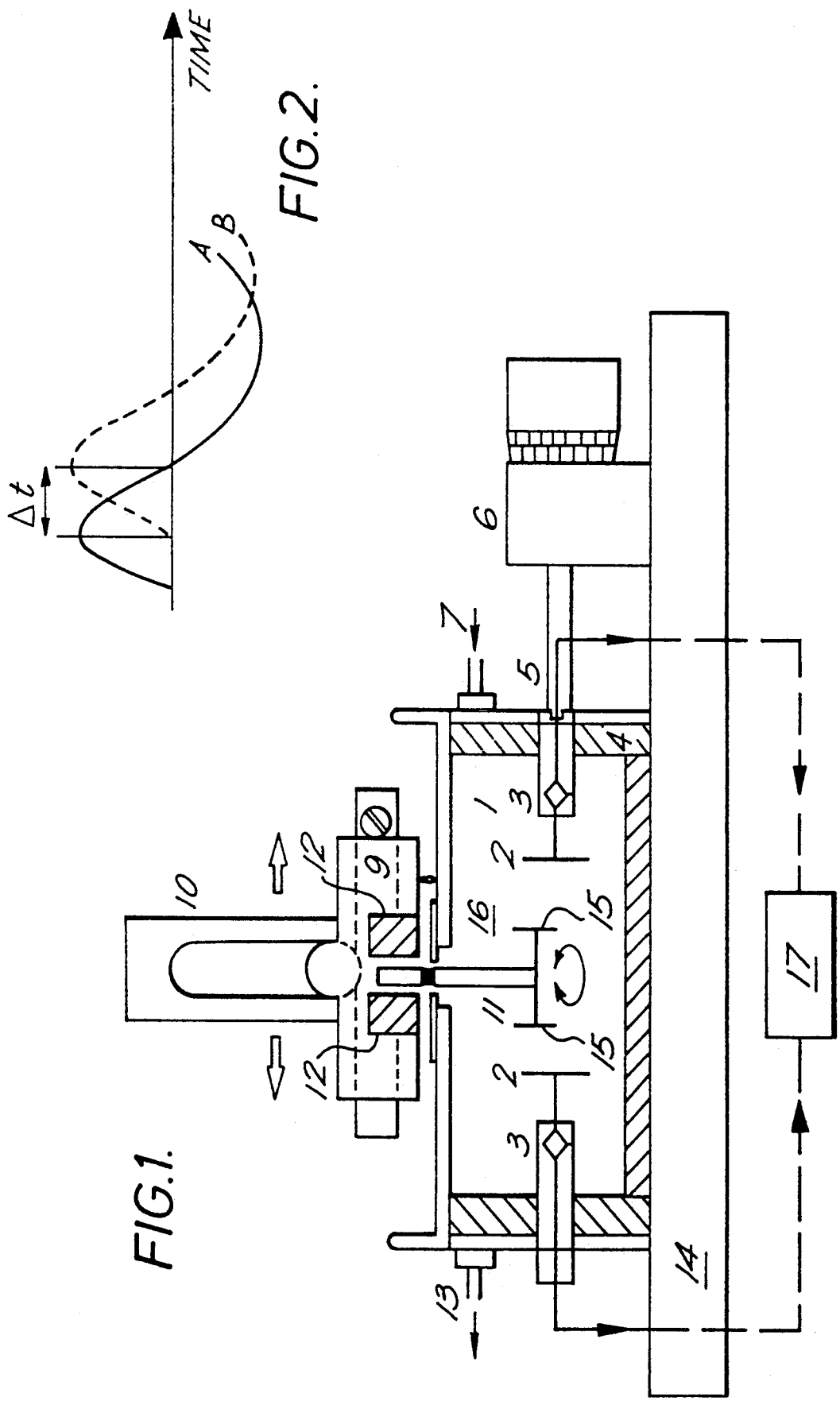

RHEOMETER

BACKGROUND OF THE INVENTION

The present invention relates to a device for investigating the properties of a viscoelastic medium, and more particularly, to a rheometer for measuring the dynamic rheological properties of gels, melts, polymer solutions, and other highly viscous media.

Conventional dynamic rheological techniques involve the forced generation of shear waves of varying magnitude in the medium under investigation and the recording of displacements of a wave-receiving and reflecting surface using a suitable transducing device. Phase and magnitude relationships between corresponding force and displacement waveforms are then analysed to determine the rheological properties of the medium. The major disadvantage of such techniques lies in the fact that accurate determination of the dynamic stresses and strains at measuring geometry boundaries is required to produce meaningful results. Such accurate determination is difficult to achieve at high frequencies.

SUMMARY OF THE INVENTION

The present invention enables a technique to be used relying on the utilisation of phase and magnitude relationships between corresponding displacement waveforms (relative to a common forcing source) generated by transducers connected to two wave receivers/reflectors disposed at different distances from the source, to determine the shear wave velocity and attenuation.

According to a first aspect of the invention, there is provided apparatus for investigating dynamic rheological properties of a viscoelastic medium comprising:
(a) a container for said viscoelastic medium;
(b) a driven member oscillatable about an axis;
(c) at least one shear wave generating surface for generating shear waves in said medium on oscillation of said driven member;
(d) a first shear wave receiving surface facing one said wave generating surface;
(e) a second shear wave receiving surface facing a second said wave generating surface, which may be the same as, or different to, said one wave generating surface, said second shear wave receiving surface being spaced from said second wave generating surface by an amount different to the spacing between said first shear wave receiving surface and said one shear wave generating surface; and
(f) at least one transducer connected to each wave receiving surface, for sensing variations in physical parameters affecting said wave receiving surfaces induced by oscillation of said driven member, and capable of generating an output signal.

Preferably two shear wave generating surfaces are provided, in which case it is preferable that each of the shear wave receiving surfaces substantially faces a respective opposed shear wave generating surface. It is further preferred that each of the shear wave generating surfaces should be substantially planar and should oscillate in a respective plane, the respective planes being substantially parallel to a corresponding substantially planar receiving surfaces.

Preferably, means for adjusting the separation between at least one of the wave generating surfaces and a respective wave receiving surface is provided. The adjusting means may be a micrometer connected to at least one of the wave generating surfaces.

It is preferred that the oscillatable member should be driven by a suitably arranged set of Helmholtz coils energised by a voltage supplied by a signal generator. It is further preferred that the voltage supplied should be sinusoidal.

The oscillations are preferably of relatively small amplitude, such that linear viscoelastic behaviour is invoked in the medium and the frequency of oscillation preferably lies in the range of 50 Hz to 3 kHz.

The transducers may be of piezo-crystal type or preferably of the non contacting inductive or capacitive type.

Further adjustment means may be provided enabling the driving member to be movable in directions substantially normal to, and substantially parallel to, the planes of the wave receiving surfaces.

It is preferred that the output signal from each transducer should be passed to signal processing means (as shown by reference numeral 17 in FIG. 1) arranged to provided a signal representative of the rheological properties of the test viscoelastic medium, determined according to computed values derived from the measured response from the respective transducers. The resulting signal may be processed by signal conditioning means for output display purposes.

According to a second aspect of the invention, there is provided a method of investigating dynamic rheological properties of a viscoelastic medium by utilising output signals from at least two transducers, each of which is connected to a respective shear wave receiving surface, which surfaces are disposed substantially within the medium under investigation such that the distance between one said receiving surface and a shear wave generation surface is different to the distance between a second said receiving surface and a corresponding shear wave generation surface.

A particular embodiment of the invention will be further described, by way of example only, with reference to the accompanying drawings in which:

BRIEF DESCRIPTION OF THE DRAWINGS

FIG. 1 is a schematic view of apparatus according to the invention;

FIG. 2 is a graphical representation of the transducer output.

DETAILED DESCRIPTION OF THE PREFERRED EMBODIMENTS

With reference to FIG. 1, a driving rod 11, which has secured to its lower end opposed shear wave generating plates 15, is attached to a jewelled bearing between a set of Helmholtz coils 12 and suspended between two steel discs 2; the latter plates are in direct contact with piezo-crystals 3 which serve to monitor deflection of the discs 2 as shear waves generated at the plates 15 impinge upon them. The coils 12 and attached rod 11 are mounted at the base of a plastics pillar 10 by a gimballed mount, allowing a wide degree of manipulation of both horizontal and vertical displacements of an electromagnetic drive assembly 9. The relative dispositions of generating plates 15 and discs 2 are achieved by micrometer positioning 5 and 6 and by the fact that the base of pillar 10 is movable relative to the test cell 1.

A voltage supplied by a signal generator (not shown) to the coils causes the rod 11 to perform small amplitude sinusoidal oscillations at controlled frequencies and displacements. Shear waves thereby generated at the plates 15 pass through the viscoelastic test medium 1 present in a chamber 16, and are detected at the surfaces of the discs 2. As the discs 2 are at unequal distances from 11 (the common source of the waves) a time-lag (or phase difference) is detected between the outputs from the piezo-crystals 3. knowledge of the unequal path lengths and time difference in arrival provides the wave velocity, as required. Calibration of transducer outputs leads to a knowledge of the relevant shear strain amplitude involved in the measurement, which may be varied by adjusting the driving voltage amplitude. The usable frequency range is 80 Hz to a few kilohertz.

Referring to FIG. 2, output waveform A is produced by the plate 15 which is nearer to rod 11, at a distance x from the rod. Output waveform B is produced by the plate which is at a larger distance $(x + \Delta x)$ away. The velocity of the shear waves v is then given by:

$$v = \Delta x / \Delta t$$

Attenuation of the shear waves is measured directly by standard techniques of noting the variation of transducer response as path length or frequency are varied. Thus, knowing v and the critical damping length, the dynamic moduli (the rigidity modulus and the loss modulus) can be obtained by known calculations.

We claim:

1. Apparatus for investigating dynamic rheological properties of a viscoelastic medium, comprising:
   (a) a container for the viscoelastic medium;
   (b) a driving member ocsillatable about an axis;
   (c) at least one shear wave generating surface supported on said driving member for generating shear waves in the viscoelastic medium upon oscillation of said driving member;
   (d) a first shear wave receiving surface arranged to be capable of facing and being spaced a first distance from one of said at least one shear wave generating surface;
   (e) a second shear wave receiving surface arranged to be capable of facing and being spaced a second distance from one of said at least one shear wave generating surface, said second distance being different from said first distance; and
   (f) a transducer connected to each wave receiving surface, for sensing variations in physical parameters affecting said wave receiving surfaces induced by oscillation of said driven member, and capable of generating an output signal.

2. Apparatus according to claim 1, which comprises two discrete said shear wave generating surfaces.

3. Apparatus according to claim 2, wherein each of the shear wave generating surfaces is substantially planar and oscillate in a respective plane, the respective plane being substantially parallel to corresponding substantially planar receiving surfaces.

4. Apparatus according to claim 3, wherein each of the shear wave receiving surfaces substantially faces a respective opposed shear wave generating surface.

5. Apparatus according to claim 3, further comprising adjusting means coupled to one of said first shear wave receiving surface, said second shear wave receiving surface and said at least one shear wave generating surface for adjusting the separation between said at least one shear wave generating surface and one of said shear first wave receiving surface and said second shear wave receiving surface.

6. Apparatus according to claim 3, further comprising adjustment means coupled to said driving member for moving said driving member in directions substantially normal to, and substantially parallel to, planes of said wave receiving surfaces.

7. Apparatus according to claim 2, wherein each of the shear wave receiving surfaces substantially faces a respective opposed shear wave generating surface.

8. Apparatus according to claim 2, further comprising adjusting means coupled to one of said first shear wave receiving surface, said second shear wave receiving surface and said at least one shear wave generating surface for adjusting the separation between said at least one shear wave generating surface and one of said shear first wave receiving surface and said second shear wave receiving surface.

9. Apparatus according to claim 2, further comprising adjustment means coupled to said driving member for moving said driving member in directions substantially normal to, and substantially parallel to, planes of said wave receiving surfaces.

10. Apparatus according to claim 1, wherein each of the shear wave receiving surfaces substantially faces a respective opposed shear wave generating surface.

11. Apparatus according to claim 10, further comprising adjusting means coupled to one of said first shear wave receiving surface, said second shear wave receiving surface and said at least one shear wave generating surface for adjusting the separation between said at least one shear wave generating surface and one of said shear first wave receiving surface and said second shear wave receiving surface.

12. Apparatus according to claim 10, further comprising adjustment means coupled to said driving member for moving said driving member in directions substantially normal to, and substantially parallel to, planes of said wave receiving surfaces.

13. Apparatus according to claim 1, further comprising adjusting means coupled to one of said first shear wave receiving surface, said second shear wave receiving surface and said at least one shear wave generating surface for adjusting the separation between said at least one shear wave generating surface and one of said shear first wave receiving surface and said second shear wave receiving surface.

14. Apparatus according to claim 13, further comprising adjustment means coupled to said driving member for moving said driving member in directions substantially normal to, and substantially parallel to, planes of said wave receiving surfaces.

15. Apparatus according to claim 1, further comprising adjustment means coupled to said driving member for moving said driving member in directions substantially normal to, and substantially parallel to, planes of said wave receiving surfaces.

16. A method of investigating dynamic rheological properties of a viscoelastic medium by utilizing output signals from at least two transducers, said method comprising:
   disposing a shear wave generation surface substantially within the viscoelastic medium;
   operatively connecting each of the transducers to a respective shear wave receiving surface, each of the transducers providing output signals; and
   disposing each of said shear wave receiving surfaces substantially within the viscoelastic medium such that the distance between one of said receiving surfaces and said shear wave generation surface is different from the distance between a second of said receiving surfaces and said shear wave generation surface, wherein the output signals of the transducers are utilized to obtain a rheological property of the viscoelastic medium.

17. A method according to claim 16, wherein said shear wave generation surface oscillates in said viscoelastic medium.

18. A method according to claim 17, wherein said shear wave generation surface oscillates generally sinusoidally at a frequency in the range 50 hz to 3 Khz.

19. A method according to claim 17, wherein the output signal from each transducer is passed to signal processing means arranged to provided a signal representative of the rheological properties of the test viscoelastic medium, determined according to computed values derived from the measured response from the respective transducers.

20. A method according to claim 18, wherein the output signal from each transducer is passed to signal processing means arranged to provided a signal representative of the rheological properties of the test viscoelastic medium, determined according to computed values derived from the measured response from the respective transducers.

21. A method according to claim 16, wherein the output signal from each transducer is passed to signal processing means arranged to provided a signal representative of the rheological properties of the test viscoelastic medium, determined according to computed values derived from the measured response from the respective transducers.

22. A method according to claim 16, further comprising: disposing a second shear wave generation surface substantially within the viscoelastic medium.

* * * * *